United States Patent [19]

Pape et al.

[11] Patent Number: 4,778,701
[45] Date of Patent: Oct. 18, 1988

[54] COMPOSITE PRELAMINATED TAPE SYSTEM

[75] Inventors: Peter H. K. Pape, Hilden; Jorg O. P. Tuschy, Kerpen, both of Minn.

[73] Assignee: Minnesota Mining and Manufacturing Company, St. Paul, Minn.

[21] Appl. No.: 867,520

[22] Filed: May 27, 1986

[51] Int. Cl.$^4$ .............................................. A61F 13/16
[52] U.S. Cl. ...................................... 428/40; 206/411; 428/41; 428/261; 428/343; 604/389; 604/390
[58] Field of Search .................. 428/261, 343, 40, 41, 428/42; 604/389, 390; 206/411

[56] References Cited

U.S. PATENT DOCUMENTS

| 3,800,796 | 4/1974 | Jacob | 128/284 |
|---|---|---|---|
| 4,051,853 | 10/1977 | Egan, Jr. | 128/287 |
| 4,066,081 | 1/1978 | Schaar | 128/287 |
| 4,074,716 | 2/1978 | Schaar | 128/287 |
| 4,237,890 | 12/1980 | Laplanche | 128/287 |
| 4,389,212 | 6/1983 | Tritsch | 604/389 |
| 4,522,853 | 6/1985 | Szonn et al. | 604/390 |

FOREIGN PATENT DOCUMENTS 54041   6/1982  European Pat. Off. .
120790  10/1984 European Pat. Off. .
2403036 4/1979  France .

Primary Examiner—George F. Lesmes
Assistant Examiner—James B. Monroe
Attorney, Agent, or Firm—Donald M. Sell; James A. Smith; Roger R. Tamte

[57] ABSTRACT

A composite adhesive closure tape comprising an assembly of sheets laminated one over the other including a central elastomeric sheet having at least one stretching axis; anchor strips disposed over the elastomeric sheet and adhered to opposite marginal end portions of the elastomeric sheet, each anchor strip having one end portion adhered to the elastomeric sheet and an unadhered end portion extending along the stretching axis in opposite directions away from the elastomeric sheet, the unadhered end portions being covered on their bottom surfaces with adhesive; a release strip underlying the elastomeric sheet, the bottom of the release strip being at least partially covered with adhesive; and an attachment sheet underlying and adhered to a portion of one of the anchor strips and underlying end adhered to the adhesive of the release strip. The composite adhesive tape may be provided in a roll or attached to the edge of a diaper.

6 Claims, 2 Drawing Sheets

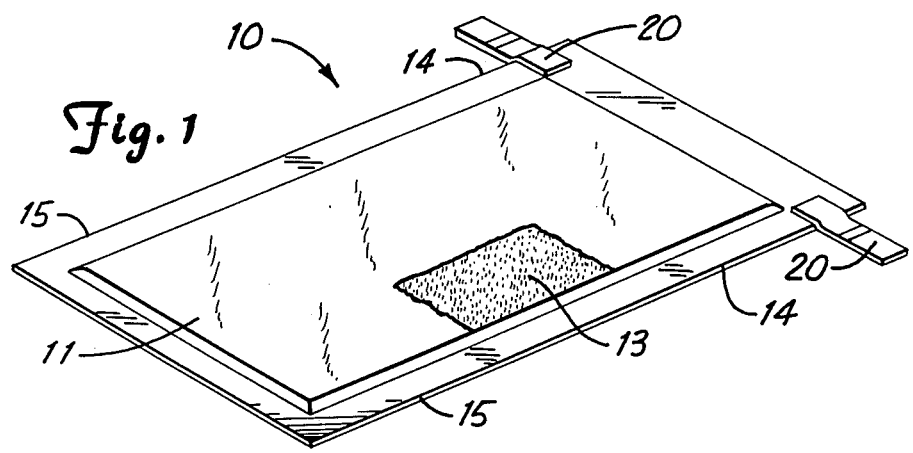
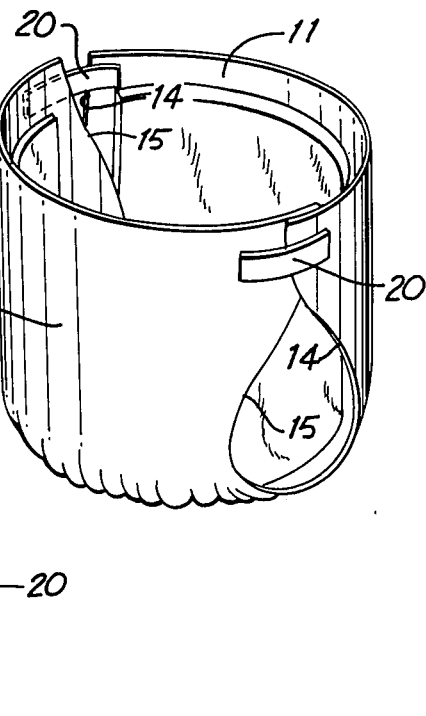
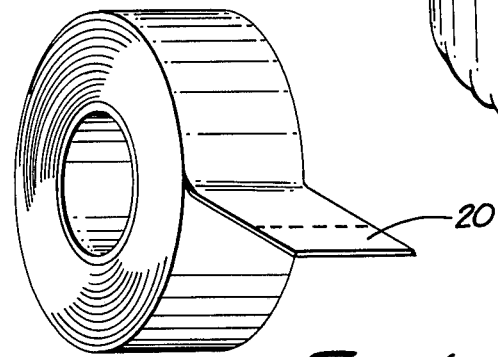

COMPOSITE PRELAMINATED TAPE SYSTEM

FIELD OF THE INVENTION

This invention relates to composite prelaminated closure systems, particularly to prelaminated tapes useful as diaper closures, wherein the closure tapes contain an elastic section, and are provided in roll form to facilitate their use in mechanized manufacturing methods, for example, in the manufacture of diapers.

BACKGROUND OF THE INVENTION

A disposable diaper typically has a thin, flexible, stretchy, low density polyethylene film cover, an absorbent filler on the inside of the cover, and a porous inner liner overlying the filler. Such a diaper is positioned at the crotch of the wearer, the two ends of the diaper extending, respectively, toward the front and back. Adjacent edges of the diaper at each side are then either positioned adjacent to each other or overlapped, a strip of pressure-sensitive adhesive tape being adhered to the cover at the border adjacent each of the two edges, holding the diaper closed.

For the comfort of the wearer it is desirable to have an elastic waistband. Heat-unstable film material has been applied to diapers to achieve an elastic waist. However, it is less expensive and easier to manufacture a diaper without the elastic waistband. In lieu of the elastic waistband, it is desirable to have an elastic closure tape.

Disposable diapers must be made at high rates of speed in order to be manufactured economically. It is thus desirable for a manufacturer of diapers to mount a single roll of closure tape containing all necessary elements directly in the line of manufacture. The closure tape is applied to the diaper as a composite tape, with the width of the roll being substantially the same as the desired length of the diaper closure to be fabricated. The closure tape is severed at right angles to the edges of the composite strip at intervals corresponding to the width of the desired closure tape and adhered at an appropriate location along the border of one side of the diaper.

Such prelaminated composite rolls must dispense the closure tape in the form of closure strips systematically and consistently in mechanized systems for manufacturing, for example, diapers. To avoid problems in manufacturing, it is necessary that the roll of closure tape be stable, which requires the tape have a generally uniform thickness throughout its width. Prior art attempts at including an elastic portion in a closure tape have resulted in a tape which creates an unstable roll, causing substantial difficulties in automated diaper production lines.

SUMMARY OF THE INVENTION

The present invention provides a composite prelaminated closure tape which can be dispensed from a stable roll form to provide a closure with a central elastomeric sheet. The closure tape can securely fasten to both sides of one edge of a sheet, for example a diaper, thereby providing greater stability to the attachment. The remaining portion of the closure tape including elastic central-portion and an anchor strip being capable of extending to and being attached to an adjacent sheet, for example, the other edge of a diaper.

The composite adhesive closure tape of the present invention comprises an assembly of sheets laminated one over the other including:

(1) a central elastomeric sheet having at least one stretching axis;

(2) first and second anchor strips disposed over the elastomeric sheet and, adhered to opposite marginal end portions of the elastomeric sheet, each anchor strip having one end portion adhered to the elastomeric sheet and an unadhered end portion extending along said stretching axis in opposite directions away from the elastomeric sheet, the unadhered end portions being covered on their bottom surfaces with adhesive to provide a fastening surface;

(3) a release strip underlying the elastomeric sheet and the fastening surface of the second anchoring strip, with the top surface of the release strip in contact with the fastening surface of the second anchor strip having release properties, and with the bottom surface of the release strip being at least partially covered with adhesive; and (4) an attachment sheet underlying and adhered to a portion of the fastening surface of the first anchor strip and underlying and adhered to a portion of the adhesive-covered surface of the release strip, whereby the release strip is attached to the assembly along an area adjacent the elastomeric sheet, with the release strip being pivotable about the area of attachment so that it can be pulled away from its position overlapping the elastomeric sheet and fastening surface of the second anchor strip and folded over to a position parallel to the fastening surface to be used to adhere a sheet between the first anchor strip and release strip.

DESCRIPTION OF THE DRAWINGS

FIG. 1 is a perspective view partially broken away to show interior detail of an open unfolded diaper.

FIG. 2 is a perspective view of the diaper of FIG. 1 in a configuration assumed by the diaper when placed about a wearer.

FIG. 6 is a perspective view of a roll of the closure tape.

DETAILED DESCRIPTION

Figure 3:
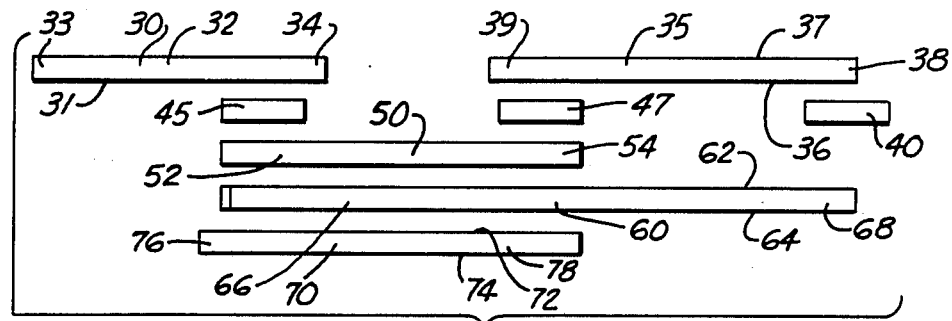
FIG. 3 is a schematic representation of a cross-section of the closure tape.

Referring first to FIGS. 1 and 2, there is shown a diaper, generally designated 10. The diaper 10 has an inside surface 11, an outside surface 12 and an absorbent filler 13. The diaper 10 has front edge portions 14 and back edge portions 15, as best shown in FIG. 2. The closure tapes attached to the front edge portions 14 are generally designated 20.

Figure 4:
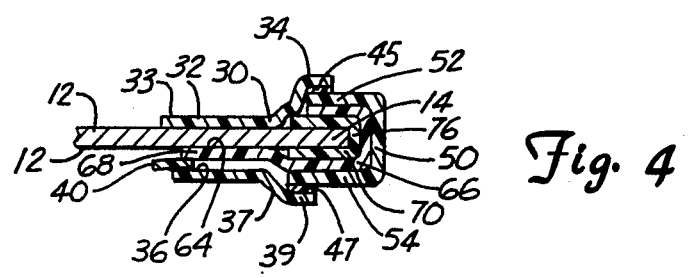
FIG. 4 is a cross-sectional view of the closure tape attached to one edge of a diaper, shown in the pre-use position.
Figure 5:
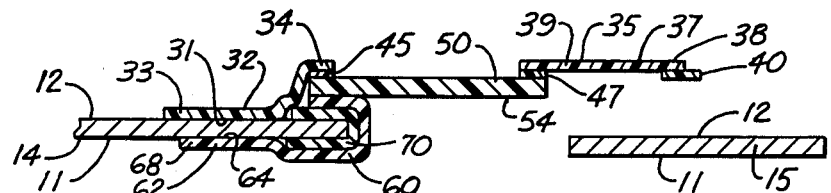
FIG. 5 is a cross-sectional view of the closure tape attached to one edge of a diaper, shown in the use position.

The details of the closure tape 20 are best shown in FIGS. 3 through 5. The closure tape 20 has a first anchor strip 30 and a second anchor strip 35. The anchor strips may comprise a material such as cloth, kraft paper, cellophane, polymeric sheets or other suitable materials or laminates thereof to which adhesive layers may be applied. Polymeric sheets which may be used include polypropylene, poly(vinylchloride), poly(ethylene terephthalate), and polyethylene. Polypropylene is presently preferred for diaper applications.

The first anchor strip 30 has a fastening surface 31 adapted to attach to the front edge portion 14 of the outside 12 of a diaper 10. The fastening surface 31 is provided with an aggressive pressure-sensitive adhesive to permanently attach the first anchor portion 30 to the diaper 10. The pressure sensitive adhesive of the fastening surface 31 will typically have a peel strength of between 7 and 10 newtons per 25 mm, preferably about 8 newtons per 25 mm, however, adhesives having other peel strength can certainly be used as desired. In order to measure peel strength of the adhesive, standard methods well known to the art such as the adhesion to a steel, polyethylene or polyester surface at 180 or 90 degrees as described hereinbelow or such as that described in U.S. Pat. No. 4,227,530 or variations thereof may be used.

The 90° peel adhesion was measured as follows: a 330-micrometer thick sheet of low density polyethylene (e.g., Eastman 1550 p-16421) is cast on a highly polished chrome roll and cooled to room temperature. Test samples approximately 80 mm×300 mm are then cut from this polyethylene sheet and a highly aggressive double-coated pressure-sensitive adhesive tape used to bond the non-shiny surface of the polyethylene to a smooth steel panel. A 25 mm×300 mm specimen of tape to be evaluated as a potential diaper closure is then obtained and the adhesive surface placed in contact with a shiny surface of the polyethylene sheet and forced into intimate contact with one forward and back pass of a mechanically operated 100 g roller. Within one minute thereafter the steel test panel is then mounted in the lower jaw of an "Instron" tensile testing machine with the tape surface upward. The free end of the tape strip is then pulled upward at 90° and mounted in the upper jaw of the tensile testing machine. The upper and lower jaws are separated at a rate of approximately 300 mm/min. noting the average force required for removal.

The first anchor strip 30 also includes a release surface 32, an unadhered edge portion 33 and an adhered edge portion 34. The release surface 32 is coated with a low surface energy material such as wax, a silicone resin or a perfluoropolymer to which pressure-sensitive adhesives will not easily adhere. Silicone resins are presently preferred because they are useful with a wider variety of adhesives and backings.

The second anchor strip 35 includes a fastening surface 36 adapted to attach to the outside 12 of the back edge portion 15 of the diaper 10 to secure the back edge portion 15 adjacent the front edge portion 14. The fastening surface 36 is preferably provided with a lower adhesion pressure sensitive adhesive to allow the second anchor strip 35 to be refastenable. Thus, typically the pressure-sensitive adhesive of the fastening surface 36 has a peel strength between about 4 to 7 newtons per 25 mm, preferably about 6 newtons per 25 mm, measured by the above described method, however, the peel strength may be varied as desired.

The second anchor strip 35 further includes a release surface 37, an unadhered edge portion 38 and an adhered edge portion 39. The release surface 37 has a release coating similar to that of the release surface 32, described above.

Attached to the unadhered edge portion 38 of the fastening surface 36 is a finger tab 40. The tab 40 is provided to allow easy removal of the second anchor strip 35 from a surface to which it is attached. The material used to make the finger tab 40 will typically be a thin film, for example, polypropylene film. An alternative embodiment does not include the finger tab 40, but instead has the marginal edge of the unadhered edge portion 38 of the fastening surface 36 free from adhesive.

The closure tape 20 further includes an elastomeric sheet 50, having a first marginal edge portion 52 and a second marginal edge portion 54. The first marginal edge portion 52 is secured to the adhered edge portion 39 of the fastening surface 31 of the first anchor strip 30 by means of an adhesive strip 45. The second marginal edge portion 54 is secured to the adhered edge portion 39 of the fastening surface 36 of the second anchor strip 35 by means of an adhesive strip 47. The elastomeric sheet 50 may be an elastomeric polyurethane film, or may be a synthetic or natural rubber. Elastomeric refers to a material which may be repeatedly stretched and returns to its original dimension after the stretching force is released. Polyurethane which is elastomeric is presently preferred. The thickness of the elastomeric sheet 50 may be 30 to 120 micrometers and is preferably about 40 to 60 micrometers. Excessive thickness in this layer can result in reduced stability of the composite roll during manufacturing.

The closure tape 20 also includes a release strip 60 and an attachment sheet 70. The release strip 60 has a release surface 62, a fastening surface 64, a secured portion, 66 and a free portion 68. The attachment sheet 70 includes a topside 72, a bottom side 74, a pivotable end 76 and an attached portion 78. The pivotal end 76 is attached to a portion of the fastening surface 31 of the first anchor strip 30. The fastening surface 64 is coated with adhesive, with the secured portion 66 of the release strip 60 attached to the top side 72 of the attachment sheet 70. The release surface 62 of the release strip 60 has release properties allowing the fastening surface 36 of the second anchor strip 35 to adhere and be pulled away from the free portion 68 of the release strip 60 as desired. The fastening surface 64 is adapted to be secured to the inside 11 of the front edge portion 14 of the diaper 10. The fastening surface 64 is typically provided with an aggressive pressure-sensitive adhesive to permanently secure it to the inside 11 of the front edge portion 14.

To accomplish this the fastening surface 64 is typically coated with a pressure-sensitive adhesive having a peel strength of between about 7 and about 10 newtons per 25 mm, preferably about 8 newtons per 25 mm, measured by the above described method, however, adhesives having varied peel strengths may certainly be used.

The pressure-sensitive adhesives coated on fastening surfaces 31, 36 and 64 may be any conventional highly elastomeric and normally tacky pressure-sensitive adhesive. Suitable adhesives include conventional rubber-based adhesives (also called rubber-resin adhesives) which have their tackiness modified by the inclusion of tackifying resins such as those described in U.S. Pat. No. 4,136,071. These resins are styrene-isoprene-styrene block copolymers which include a minor amount of styrene-isoprene blocks and are tackified with synthetic polyterpene.

The attachment sheet 70 prevents the fastening surface 64 of the release strip 60 from adhering to the elastomeric strip 50 when the tape is in the roll form. The attachment sheet 70 is therefore positioned to extend between the adhered edge portions 34, 39 of the anchor strips 30, 35. The attachment sheet 70 adhered to the fastening surface 31 achieves better load distribution when the closure tape 20 is used to secure a diaper as described below.

A closure tape of the invention has at least one stretching axis, which is parallel to the plane of the sheet on which FIG. 3 is drawn, or lengthwise of the closure tapes 20 as shown on the diaper 10 in FIG. 2. Closure tapes of the invention can be cut from a stock material wound in a roll in which case the described stretching axis is transverse to the length of the stock material. In use, a segment of a roll of closure tape 20 is cut from the roll in a desired width; see FIG. 6 which shows the dotted line along which the tape is cut. Thereupon, the fastening surface 31 of the first anchor strip 30 is secured to the outside 12 of the front edge portion 14 of a diaper 10 as shown in FIG. 4. The attachment sheet 70 and the release strip 60 are folded around the front edge portion 14 and the free end 68 of the fastening surface 64 is secured to the inside 11 of the front edge portion 14. The second anchor strip 35 is folded around the diaper 10 and adhered to the release surface 62 of the free end 68. The tape is now in the pre-use position as shown in FIG. 4. It is contemplated that a diaper would be sold to the consumer in this condition.

In use, a diaper 10 containing the tape 20 of the present invention is positioned around a wearer, as shown in FIG. 2. To secure the front edge portion 14 to the back edge portion 15 the finger tab 40 is grasped and the fastening surface 36 is pulled away from the release surface 62. The fastening surface 36 is then secured to the outer cover 12 of the back edge portion 15. When the same process is followed on the other side of the wearer, the diaper is then secured in place with the elastomeric sheet 50 provided a flexible connection between the front edge portion 14 and the rear edge portion 15 of the diaper 10.

What is claimed is:

1. A roll of laminated strips from which a composite adhesive closure tape may be cut comprising:
   (1) a central elastomeric sheet having at least one stretching axis transverse to the longitudinal length of the sheet;
   (2) first and second anchor strips disposed over said elastomeric sheet and adhered to opposite marginal edge portions of the elastomeric sheet, each anchor strip having one edge portion adhered to said elastomeric sheet and an unadhered edge portion of each of said anchor strips extending along said stretching axis in opposite directions away from said elastomeric sheet, the unadhered end portions being covered on their bottom surfaces with adhesive to provide a fastening surface, and having top surfaces of low surface energy material to provide release surfaces;
   (3) a release strip underlying said elastomeric sheet and said fastening surface of said second anchoring strip, with the top surface of said release strip in contact with said fastening surface having release properties, and with the bottom surface of said release strip being at least partially covered with adhesive; and
   (4) an attachment sheet underlying and adhering to a portion of said fastening surface of said first anchor strip and underlying and adhered to a portion of the adhesive-covered surface of said release strip, whereby said release strip is attached to the assembly along an area adjacent said elastomeric sheet;
wherein in the roll form the release surface of the first anchor strip is adjacent to and protects that portion of the fastening surface of the first anchor strip unadhered to the attachment sheet and the elastic strip, the release surface of the second anchor strip is adjacent to and protects that portion of the bottom surface of the release strip unadhered to the attachment sheet, and the attachment sheet is adjacent to and protects the surface of the elastomeric sheet that lies between said sheet's edge portions adhered to said anchor strips.

2. The roll of claim 1 wherein said adhesive of said first anchor strip has a greater peel strength that said adhesive of said second anchor strip.

3. The roll of claim 2 wherein said adhesive of said first anchor strip has a peel strength greater than 7 newtons per 25 mm.

4. The roll of claim 3 wherein said adhesive of said second anchor strip has a peel strength of less than 7 newtons per 25 mm.

5. The roll of claim 1 and also including adhesive portions adhering said anchor strips to said elastic sheet.

6. The roll of claim 1 wherein the marginal edge of said unadhered end portion of said second anchor strip is free from adhesive.

* * * * *

UNITED STATES PATENT AND TRADEMARK OFFICE
CERTIFICATE OF CORRECTION

PATENT NO. : 4,778,701

DATED : October 18, 1988

INVENTOR(S) : Peter H.K. Pape and Jorg O.P. Tuschy

It is certified that error appears in the above-identified patent and that said Letters Patent is hereby corrected as shown below:

On the Title Page, Column [75], "both of Minnesota" should read --both of Federal Republic of Germany--.

Signed and Sealed this

Twenty-eighth Day of February, 1989

Attest:

DONALD J. QUIGG

*Attesting Officer*     *Commissioner of Patents and Trademarks*